(12) United States Patent
Fish

(10) Patent No.: US 9,228,947 B2
(45) Date of Patent: Jan. 5, 2016

(54) DEVICE FOR MONITORING A PLURALITY OF DISCRETE FLUORESCENCE SIGNALS

(75) Inventor: David Andrew Fish, Haywards Heath (GB)

(73) Assignee: KONINKLIJKE PHILIPS N.V., Eindhoven (NL)

(*) Notice: Subject to any disclaimer, the term of this patent is extended or adjusted under 35 U.S.C. 154(b) by 412 days.

(21) Appl. No.: 13/502,628

(22) PCT Filed: Oct. 18, 2010

(86) PCT No.: PCT/IB2010/054709
§ 371 (c)(1),
(2), (4) Date: Apr. 18, 2012

(87) PCT Pub. No.: WO2011/048539
PCT Pub. Date: Apr. 28, 2011

(65) Prior Publication Data
US 2012/0208263 A1 Aug. 16, 2012

(30) Foreign Application Priority Data
Oct. 23, 2009 (EP) .................................... 09173971

(51) Int. Cl.
*C12M 1/34* (2006.01)
*G01N 21/00* (2006.01)
(Continued)

(52) U.S. Cl.
CPC .......... *G01N 21/6428* (2013.01); *C12Q 1/6874* (2013.01); *G01N 21/6452* (2013.01); *G01N 2021/6421* (2013.01)

(58) Field of Classification Search
CPC .......... G01N 21/6428; G01N 21/6452; G01N 2021/6421; C12Q 1/6874
USPC .................................... 435/287.2, 288.7, 808
See application file for complete search history.

(56) References Cited

U.S. PATENT DOCUMENTS

| 5,059,814 A | 10/1991 | Mead |
| 5,561,287 A | 10/1996 | Turner |

(Continued)

FOREIGN PATENT DOCUMENTS

| EP | 0744624 A2 | 11/1996 |
| JP | 11023532 A | 1/1999 |

(Continued)

OTHER PUBLICATIONS

Nishimura, N. et al "A CMOS Optical Sensor which Counts the Number of Objects" Transactions of The Institute of Electrical Engineers of Japan, Part E, vol. 120-5, No. 5, 2000 Abstract Only.
(Continued)

*Primary Examiner* — Nathan Bowers

(57) ABSTRACT

The present invention relates to a device and detector for monitoring a plurality of discrete fluorescence signals, in particular for DNA sequencing by use of fluorescently labeled nucleotides. The particular detector (118) is proposed comprising a plurality of pixels (130) for individually detecting said fluorescence signals from the plurality of fluorescent signal sources (104), wherein each pixel (130) comprises a predetermined number of at least two detection elements (D1, Dn) for detecting a received fluorescent signal and for generating detection signals. Further, a signal conversion circuit (140) is provide for receiving said detection signals from said at least two detection elements (D1, Dn) and for generating a pixel output signal indicating which of said at least two detection elements (D1, Dn) generated the strongest detection signal.

20 Claims, 8 Drawing Sheets

(51) Int. Cl.
   *G01N 21/64* (2006.01)
   *C12Q 1/68* (2006.01)

(56) References Cited

U.S. PATENT DOCUMENTS

| | | | |
|---|---|---|---|
| 6,046,466 A * | 4/2000 | Ishida et al. | 257/258 |
| 6,362,662 B1 | 3/2002 | Shi | |
| 7,148,460 B2 * | 12/2006 | Moses et al. | 250/214 R |
| 2007/0188750 A1 | 8/2007 | Lundquist | |
| 2007/0206187 A1 * | 9/2007 | Lundquist et al. | 356/318 |
| 2008/0251730 A1 * | 10/2008 | Ballabriga et al. | 250/370.09 |
| 2009/0197326 A1 * | 8/2009 | El Gamal et al. | 435/287.2 |

FOREIGN PATENT DOCUMENTS

| | | |
|---|---|---|
| WO | 2004059006 A1 | 7/2004 |
| WO | 2007119067 A1 | 10/2007 |
| WO | 2008140758 A1 | 11/2008 |
| WO | 2009089056 A1 | 7/2009 |

OTHER PUBLICATIONS

Yu, Haiming et al "A High-Speed and High-Precision Winner-Select-Output (WSO) ASIC", IEEE Transactions onNuclear Science, vol. 45, No. 3, Jun. 1998, pp. 772-776.

"Pacific Biosciences Develops Transformative DNA Sequencing Technology", Pacific Biosciences Technology Backgrounder, 2008, pp. 1-12.

Moses, W.W. et al "A 'Winner-Take-All' IC for Determining the Crystal of Interaction in PET Detectors", IEEE Transactions on Nuclear Science, vol. 43, pp. 1615-1618, 1996.

Oki, Nobuo "Winner-Take-All Circuit using CMOS Technology" Circuits and Systems, 1998, Proceedings, Midwest Symposium on Volume, Issue 9-12, pp. 568-570.

* cited by examiner

DEVICE FOR MONITORING A PLURALITY OF DISCRETE FLUORESCENCE SIGNALS

FIELD OF THE INVENTION

The present invention relates to a device for monitoring a plurality of discrete fluorescence signals, in particular for DNA sequencing by use of fluorescently labeled nucleotides.

The present invention relates further to a detector for detecting fluorescence signals from a plurality of fluorescence signal sources for use in such a device for monitoring a plurality of discrete fluorescent signals.

BACKGROUND OF THE INVENTION

DNA (deoxyribonucleic acid) sequencing has been known for many years. The basic concept of identifying the building blocks of the nucleic acid, containing genetic instructions used in the development and functioning of all known living organisms, has been extended from the discovery of codes to the desire to use genetic information to tackle disease.

The main role of DNA molecules is the long term storage of information. Among other functions, it contains instructions needed for construction of components of cells, in segments referred to as genes. Chemically, DNA consists of two long polymers of simple units called nucleotides, the two strands running in opposite directions to each other. Backbones between the two strands are made of sugars and phosphate groups joined by ester bonds. Attached to each sugar is one of four types of molecules called bases, of type A, C, G or T. It is the sequence of these four bases along the backbone which encodes information. By identification of these bases and their sequence, much information can be derived.

Many of the new techniques rely on fluorescent imaging for identification of the bases, known as base calling. A fluorescent moiety is attached to one particular kind of base. The fluorescence in the nucleotide is effected by absorption of light at known wavelength. The fluorescence occurs at another, slightly different, known wavelength. Detection of the fluoresced light indicates the presence of a particular base. Single color fluorescent systems exist wherein different fluids comprising sequencing reagents are washed over a sample in succession and fluorescence indicates the presence of different DNA bases in the DNA sample. Another fluorescent imaging technique is known as four color fluorescence as four different wavelengths of light are used, thereby permitting four types of nucleotide (needed for sequencing reactions) to be present in the sequencing device at the same time. Thus fluid exchanges in the device (which are very slow) can be reduced or kept to a minimum.

Methods and systems for analyzing fluorescent materials relying on fluorescence imaging for base calling are described by Pacific Biosciences, in particular in Pacific Biosciences technology backgrounder "Pacific Biosciences develops transformative DNA sequencing technology", Feb. 2, 2008, and in their patent applications WO 2008/140758 A1 and WO 2009/089056 A1. Light emitted by fluorophores is collected by a high numerical aperture objective lens and brought to a focus on a single-photon sensitive CCD array. Before reaching the array, the light passes through a prism dispersive element that deflects the fluorescent light according to its color, creating an individual rainbow for each zero mode waveguide. This allows the position of the deflective light to encode the identity of the base that produced the signal. In this way a single high-sensitive detector can be used to both identify and discriminate the pulses according to the position they strike the CCD array. This process is repeated thousands of times over the area of the CCD array, enabling the DNA sequence to be read in real time in each zero mode waveguide across the entire single-molecule real time chip. An optimized set of algorithms is used to translate the information that is captured by the optics system. Using the recorded spectral information and pulse characteristics, signals are converted into base calls with associated quality metrics.

However, there are also limitations with this technology, mainly based due to the kind of detector that is used. With the EMCCD (Electron Multiplying Charge Coupled Device) detector that is used high field rates can only be attained when the number of pixels is small. In practice, however, a large number of pixels is required to read out very high numbers of sequencing sites, e.g. one million of sequencing sites or more. Further, a high field rate is required to keep up with reaction rates, which can be expected to increase in the future to 1 kHz. Such performance is well beyond the capabilities of the CCD technology.

SUMMARY OF THE INVENTION

It is an object of the present invention to provide a device for monitoring a plurality of discrete fluorescence signals that is improved compared to the known devices and which particularly enables to the simultaneously read out a large number of pixels at a higher field rate. It is a further object of the present invention to provide a corresponding detector for use in such a device.

In a first aspect of the present invention a device for monitoring a plurality of discrete fluorescence signals is provided, in particular for DNA sequencing by use of fluorescently labeled nucleotides, comprising:
  a substrate having a plurality of discrete fluorescent signal sources disposed thereon;
  an excitation illumination source;
  a detector for detecting fluorescent signals from the plurality of fluorescent signal sources; and
  an optical train positioned to simultaneously direct excitation illumination from the excitation illumination source to said plurality of discrete fluorescent signal sources on the substrate, and to direct fluorescent signals from the plurality of fluorescent signal sources to the detector,
  wherein said detector comprises
  a plurality of pixels for individually detecting said fluorescent signals from the plurality of fluorescent signal sources, each pixel comprising a predetermined number of at least two detection elements for detecting a received fluorescent signal and for generating detection signals and
  a signal conversion circuit for receiving said detection signals from said at least two detection elements and for generating a pixel output signal indicating which of said at least two detection elements generated the strongest detection signal.

In a further aspect of the present invention a detector for use in such a device is provided, said detector comprising
  a plurality of pixels for individually detecting said fluorescence signals from the plurality of fluorescence signal sources, each pixel comprising a predetermined number of at least two detection elements for detecting a received fluorescent signal and for generating detection signals and
  a signal conversion circuit for receiving said detection signals from said at least two detection elements and for generating a pixel output signal indicating which of said at least two detection elements generated the strongest detection signal.

Preferred embodiments of the invention are defined in the dependent claims. It shall be understood that the claimed detector has similar and/or identical preferred embodiments as the claimed device and as defined in the dependent claims.

The present invention is based on the idea to generally apply the same system layout as proposed by Pacific Biosciences, in particular comprising a substrate, an excitation illumination source, a detector and an optical train, and to use the dispersion based method for fluorescence detection, but to use a different detector to enable a large number of pixels to be read out at high field rates. The known dispersion method of determining base incorporation into DNA requires, for instance, approximately 15 detection elements (e.g. photodiodes) of the CCD array. To enable separation between the sequencing reactions a minimal CCD area of about 16×4 detection elements would be required. According to the present invention, instead of reading out all 64 (or at least 15) analog values from the detection elements representing one pixel of the detector, a single pixel output signal is generated that represents the incorporated base.

In particular, according to the present invention a signal conversion circuit is provided to which the detection signals from a number of detection elements representing a single pixel and receiving a fluorescence signal from a single fluorescent signal source are provided, which signal conversion circuit then converts said number of detection signals into said single pixel output signal. Said pixel output signal is generated from the input detection signals such that it indicates which of the at least two detection elements that are coupled to the single signal conversion circuit generated the strongest detection signal.

Hence, the position of the detection element that generated the strongest detection signal within a pixel is known which inherently incorporates the information about the identity of the fluorescent signal source. For instance, if applied for DNA sequencing by use of fluorescently labeled nucleotides the identity of the base that produced the fluorescent signal is included in the pixel output signal since the position of the detection element that generated the strongest detection signal correlates with the fluorescent label and, hence, with the base since the various types of bases (A, G, C, T) are differently labeled.

Since according to the present invention only a single value is to be read out from each pixel rather than, for instance, 15 or more values as in the known devices, the readout rate can be massively enhanced which enables the sequencing reactions to occur more rapidly, e.g. by increased concentrations of nucleotides and higher temperatures, and more reactions could be performed in parallel. This strongly improves the throughput of the device and enables whole genome and gene re-sequencing applications to be performed very rapidly.

Particularly for use in DNA sequencing each pixel comprises preferably at least four, in particular between eight and sixteen, detection elements to get a higher resolution and accuracy for the detection of which base caused the fluorescent signal. The number of detection elements, e.g. photodiodes within a CCD array, can also be higher depending on the desired resolution and accuracy.

Preferably, the signal conversion circuit is adapted for generating a digital pixel output signal which can be easily and quickly read out. Preferably if the plurality of pixels is arranged as an array along columns and rows, as proposed according to a further embodiment, the detector further comprises addressing and readout means for individually addressing and reading out said pixel output signals from said pixels.

The use of a digital pixel output signal is preferred. Such an array structure is, for instance, known from semiconductor memory devices, and similar row and column addressing and read out means known from semiconductor memory technology can be applied here. For instance, the digital pixel output signal can be a binary 4-bit signal, said 4 bits encoding the position of the detection element (of 16 detection elements of a pixel) having the strongest detection signal.

The present invention preferably uses CMOS technology by which the signal conversion circuit can be advantageously implemented on a detector. For individually addressing each detection element a selection switch is preferably provided for each detection element, which is particularly realized by a N-type MOSFET transistor, wherein said selection switch can be switched on and off by use of a selection switch addressing signal for enabling the forwarding of the output signal generated by the associated detection element to the associated signal conversion circuit. During the detection this selection switch is generally switched off, but at the end of the detection period the selection switches for all detection elements of a pixel are switched on so that the detection signals of all detection elements of a pixel are simultaneously provided to the signal conversion circuit for further processing and finding which detection element generated the strongest detection signal and generating a corresponding pixel output signal.

According to another embodiment the addressing and readout means comprises a reset switch for each detection element, in particular a N-type MOSFET transistor, which can be switched on and off by use of a reset signal for resetting the detection element after each detection period.

According to still another embodiment an addressing and readout means comprises a voltage-to-current conversion element for each detection element for converting the detection signal of said detection element into a detection current signal. Said voltage-to-current conversion element is preferably realized by a P-type MOSFET transistor whose gate is coupled to the output of the associated detection element. Hence, the detection signal outputted from the detection element controls the voltage-to-current conversion element which outputs more current if the detection element increases. This provides a simple but effective way of implementing the voltage-to-current conversion.

For generating the pixel output signal from the inputted detection signals the signal conversion circuit preferably comprises a winner take all circuit. Such winner take all circuits are generally known in the art, for instance from Moses et al., "A "winner take all" IC for Determining the Crystal Interaction in PIT Detectors", IEEE Trans. Nuclear Science, vol. 43, pp. 1615, 1996 or Oki, N., "Winner-Take-All Circuit Using CMOS Technology", Circuits and Systems, 1998, Proceedings, 1998, Midwest Symposium on Volume, issue 9-12 Aug. 1998, pp. 568-570. Various embodiments of such a winner take all circuit exist which can generally all be applied here for signal conversion. Such a circuit receives in parallel the detection signals from all coupled detection elements of a single pixel and has a corresponding number of intermediate output lines, i.e. one intermediate output line for each detection element. However, such a winner take all circuit is adapted such that due to a chain reaction only on one single intermediate output line a high signal output, in particular a high current, is obtained which corresponds to the detection signal that emitted the strongest detection signal, whereas on the other intermediate output lines a low output signal, in particular a small output current, is detected. These intermediate output lines are coupled to a common output line which is read out, for instance sequentially or in parallel, to obtain the desired, preferably digital, pixel output signal.

According to a preferred embodiment the winner take all circuit comprises, for each connected detection element, a first N-type MOSFET transistor, whose drain terminal is provided with the a detector current signal representing the detection signal detected by said detection element, whose source terminal is coupled to a reference potential, in particular ground potential, and whose gate terminal is provided with a predetermined bias current, and a second N-type MOSFET transistor, whose gate terminal is coupled to the drain terminal of the first N-type MOSFET transistor, whose source terminal is coupled to the gate terminal of the first N-type MOSFET transistor and is provided with said predetermined bias current and whose drain terminal is outputting a detector element output signal.

The winner take all circuits can either be arranged external to the area of the plurality of pixels or within the area of the plurality of pixels, in particular in the area of the associated pixels. But it is also possible that there are for each pixel two winner take all circuits, wherein a first winner take all circuit is arranged external to the area of the plurality of pixels and a second winner take all circuit is arranged within the area of the plurality of pixels (130), in particular in the area of the associated pixels.

As mentioned above the general layout of the device can be as described by

Pacific Biosciences as regards the excitation illumination source, the substrate having a plurality of discrete fluorescence signal sources disposed thereon and the optical train. Hence, according to a preferred embodiment the optical train comprises an objective lens focused in a first focal plane at the substrate, for simultaneously collecting fluorescent signals from the plurality of fluorescent signal sources on the substrate, a spectral separation means for spatially separating spectral components of the fluorescence signals, and a focusing lens for receiving the spatially separated spectral components of the fluorescent signals and focusing them onto the detector.

BRIEF DESCRIPTION OF THE DRAWINGS

These and other aspects of the invention will be apparent from and elucidated with reference to the embodiment(s) described hereinafter. In the following drawings

DETAILED DESCRIPTION OF THE INVENTION

For DNA sequencing various systems and methods are known. In a particular exemplary system, individual DNA polymerase/template/primer complexes, immobilized on a solid support, are illuminated with excitation light while they incorporate fluorescently labeled nucleotide analogs. Characteristic fluorescent signals emanating from these individual complexes indicate whether a given nucleotide is incorporated by the complex. In some methods, labeled nucleotides are actually incorporated while still bearing the fluorescent label group. Unincorporated labeled nucleotides are then washed away from the immobilized complex and the complex is illuminated and fluorescent signals monitored to determine the presence of an incorporated fluorescent nucleotide. The fluorescent label is then removed from the incorporated nucleotide and washed from the system. A second nucleotide is contacted with the complex and its incorporation or lack thereof, is monitored in the same fashion. In some aspects, these systems employ a single type of nucleotide in each step, requiring a cycled process of interrogating the complex with each of the four types of nucleotides.

In another system, a polymerase/template/primer complex is provided within a confined illumination volume that localizes the illumination to the area including a single complex and not much more. As labeled nucleotides are incorporated by the complex, they are retained within the illumination volume for periods longer than the average diffusion time of unincorporated nucleotides, thus giving a characteristic optical signal associated with that incorporation. Further, by employing nucleotides that bear the fluorescent label on the beta, gamma or more distal phosphate group of a nucleoside polyphosphate, the label group is automatically cleaved during incorporation. The result is that following the characteristic incorporation fluorescent signal, the label group is released to behave more like randomly diffusing nucleotides. As a further result, one is able to monitor nucleotide incorporations in real time as they occur. By labeling each type of nucleotide (e.g., A, G, C and T) with a spectrally distinguishable fluorescent label or dye and monitoring the reaction for the different fluorescent signals, one can not only identify an incorporation event, but also identify the type of nucleotide incorporated.

Figure 1:
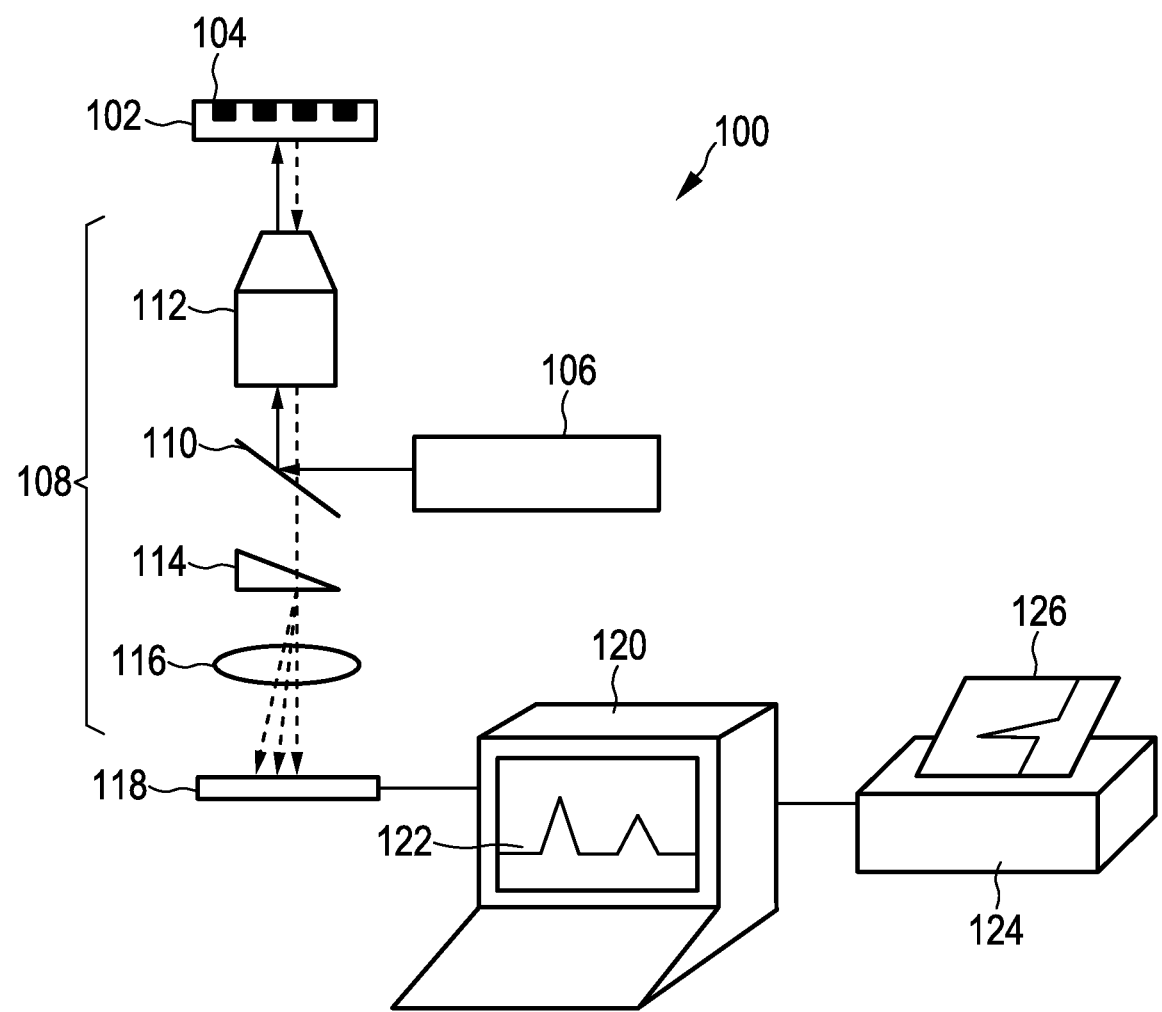
FIG. 1 shows a schematic diagram of a fluorescence detection device according to the present invention.

An exemplary fluorescence detection device, in which the present invention can be applied, is schematically illustrated in FIG. 1. As shown, the device 100 includes one or more excitation illumination sources, i.e., laser 106. The excitation light from laser 106 is directed to a reaction region, e.g., reaction region or well 104 on substrate 102, by the optical train 108. Although optical trains may vary depending upon the desired application, as shown, the excitation beam from laser 106 is directed at and reflected by a dichroic mirror 110, and passed into objective lens 112, which focuses the excitation beam onto the reaction region/well 104 of substrate 102. Fluorescent signals emitted from the reaction regions in response to the excitation beam are then collected by objective lens 112, and, by virtue of their shifted wavelength relative to the excitation beam, are transmitted through dichroic mirror 110. The fluorescent signal is then focused by focusing lens 116 onto a detector 118, which registers the incident signal thereon.

As shown, the fluorescent signal may also be subjected to spectral separation to separate out spectrally different signal components that emanate from different reactions or different events in the same reaction. As shown, spectral separation is accomplished by passing the fluorescent signal through a dispersive optical element, such as wedge prism 114 to direct spectrally different signals or signal components to different regions of the detector 118.

Signals received by the detector 118 are then recorded and processed by a processor such as computer 120, and displayed in a convenient user friendly format, e.g., display 122 or printout 126 from printer 124.

More details about the layout, implementation and function of such a device in general as well as about fluorescence based detection for DNA sequencing can be found in WO 2008/1407588 A1, WO 2009/089056 A1 and the above cited technology backgrounder of Pacific Biosciences, to which reference is herewith made and which details are herein incorporated by reference.

Figure 2:
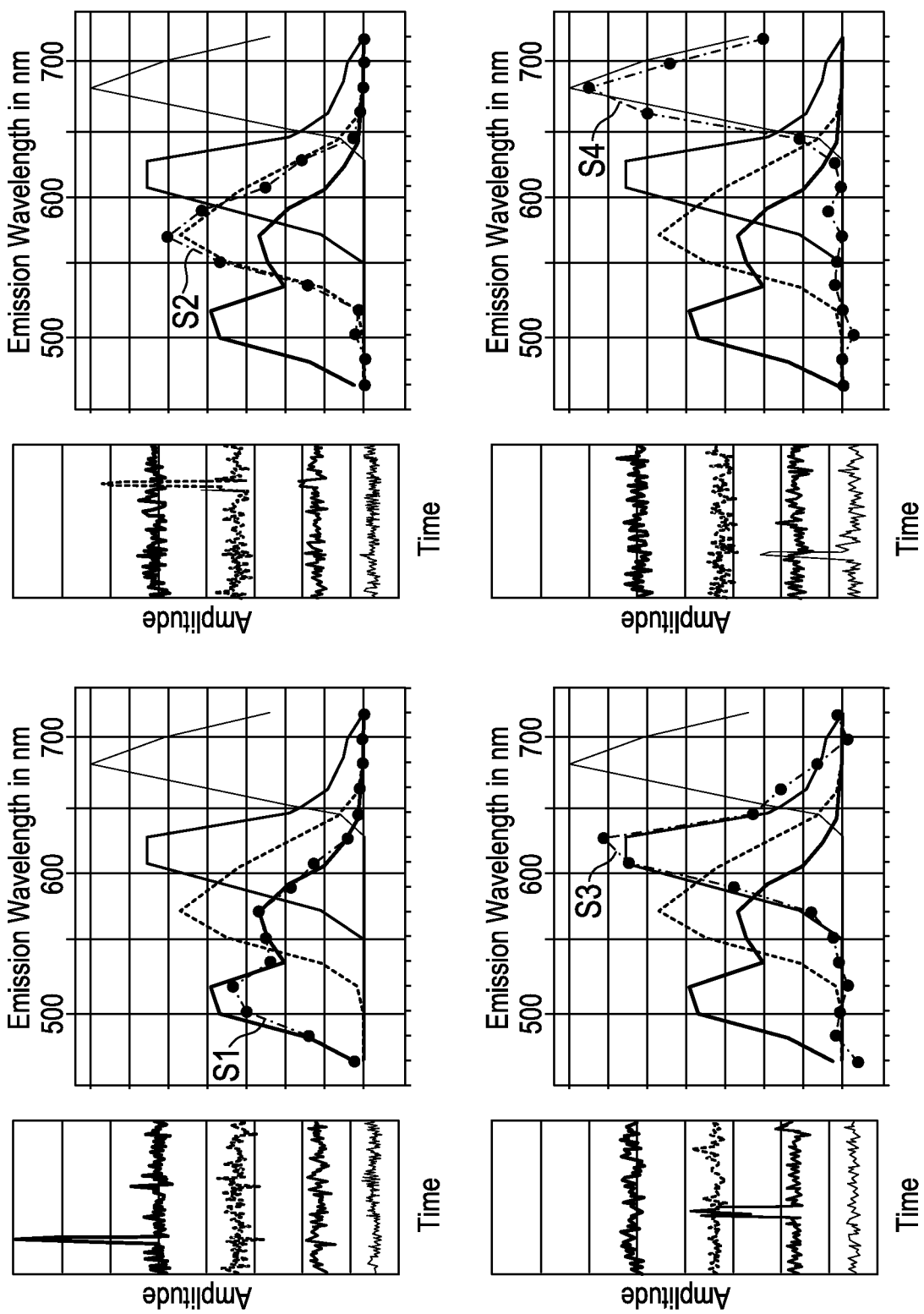
FIG. 2 shows a diagram illustrating typical detection signals over time and corresponding spectra.

Typical detection signals over time and their spectra collected from one observation volume at different times are shown in FIG. 2. The four time signals recorded at each time are taken from a different spectral channel of a multi-component analysis of the dispersed light collected from the observation volume. In the spectral plots, the solid curves represent reference spectra collected from each of the four fluorophores in a calibration process. In each plot the signal curve (indicated by S1 to S4) with error bars represents the photon flux integrated over the duration of the burst as a function of relative spectral position. The shown fluorescence bursts represent integrated burst SNR ratios between 20 and 35. Hence, by comparing the spectrum of the measured signal with those reference spectra the fluorophore, by which the nucleotide is labeled and that caused the fluorescent signal, can be easily found.

Figure 3:
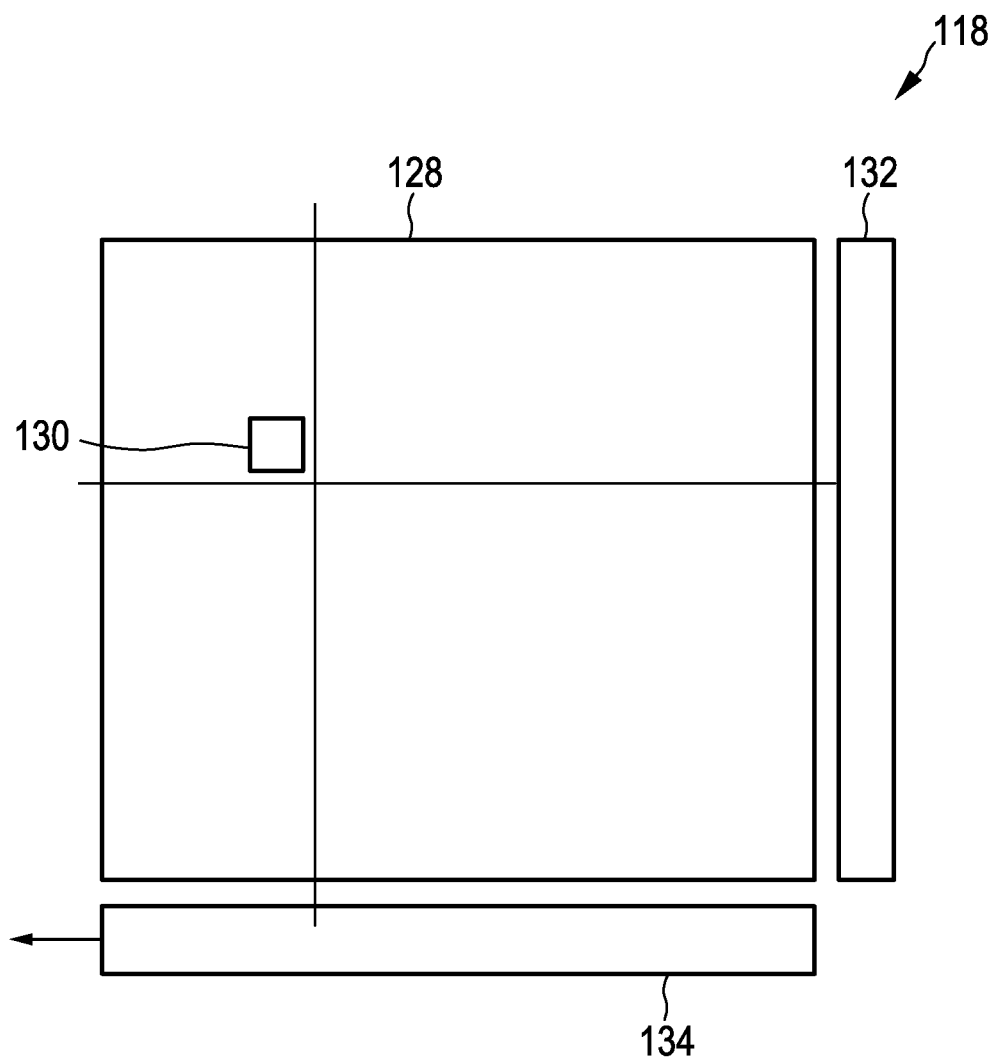
FIG. 3 illustrates a general layout of a detector according to the present invention.

The general layout of the detector used according to the present invention, in particular in the system shown in FIG. 1 as the detector 118, is illustrated in FIG. 3. The detector 118 comprises an array 128 of a plurality of pixels 130 arranged along rows and columns, as, for instance, known from the memory elements of a semiconductor memory device, e.g. a DRAM memory device. For addressing, switching and resetting purposes, i.e. for individually addressing, resetting and/or switching individual pixels and/or individual detection elements of the pixels, appropriate addressing and readout means are provided as generally also known from semiconductor memory technology. In particular, in the embodiment illustrated in FIG. 3, said addressing and readout means comprises a row driver unit 132 and a column driver unit 134. The row driver unit 132 particularly fulfills the function of row selection, i.e. individually addressing the pixels and/or detection elements of a particular row within the array 128 as well as resetting the pixels and/or detection elements within a particular row. The column driver unit 134 particularly serves the purpose of individually reading out the detection signals from the individual detection elements of pixels within a column and for converting the detection signals of detection elements of a pixel into the single pixel output signal. If needed, this pixel output signal can then be further processed or outputted directly.

Figure 4:
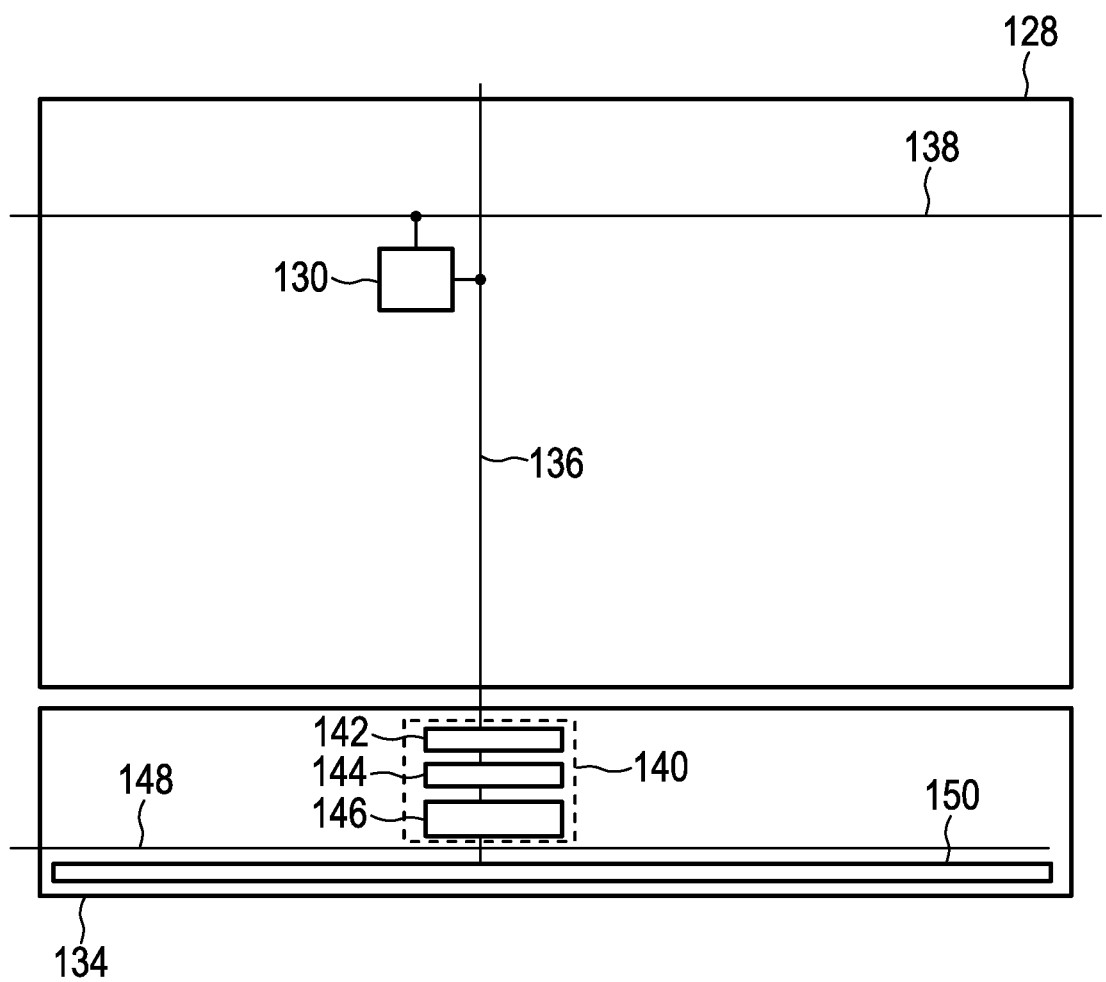
FIG. 4 shows a diagram illustrating more details of the exemplary layout of the detector according to the present invention.

More details, particularly of an embodiment of the column driver unit 134, are shown in FIG. 4. As an exemplary embodiment it shall be assumed that a pixel 130 comprises 16 detection elements so that 16 detection signals are outputted from said detection elements.

These detection signals are, eventually after some preprocessing as will be illustrated below, outputted over a 16 line column bus 136 (provided said particular pixel is addressed by an appropriate addressing signal via the connected row bus 138) to the column driver unit 134. The column driver unit 134 comprises, for each column (or in a more advanced embodiment, for each pixel), a signal conversion circuit 140 for receiving the detection signals from all the detection elements of a pixel 130 that is currently read out (as controlled via the row bus 138) and for generating the pixel output signal.

The signal conversion circuit 140 comprises, in this exemplary embodiment, a winner take all circuit 142, a digital conversion circuit 144 and a register 146. The winner take all circuit 142 receives the (in this example 16) detection signals and outputs a corresponding number of intermediate output signals. Due to the chain reaction, as further explained below in detail, only one of said intermediate output signals is a signal having a high output amplitude, whereas the other intermediate output signals have a low output amplitude. These intermediate output signals are provided to the digital conversion circuit 144 which converts said intermediate output signals into a digital signal. For instance, in case of 16 output signals a binary 4-bit digital pixel output signal is generated into which the information is encoded which of said 16 intermediate output signals had the high amplitude and which thus also indicates which of said 16 detection elements of the pixel 130 outputted the strongest detection signal. Said pixel output signal is then forwarded to a register 146 for storage until it can be outputted on the data output bus 148.

Within the column driver unit 134 there will be N registers 146 (in case of N columns) holding digital data. Generally, however, only one register 146 can be read out at a time. Hence, in a preferred embodiment an additional shift register 150 is provided which selects which register 146 to read out. It is called a shift register because it shifts the selection point one place every clock cycle.

Figure 5A:
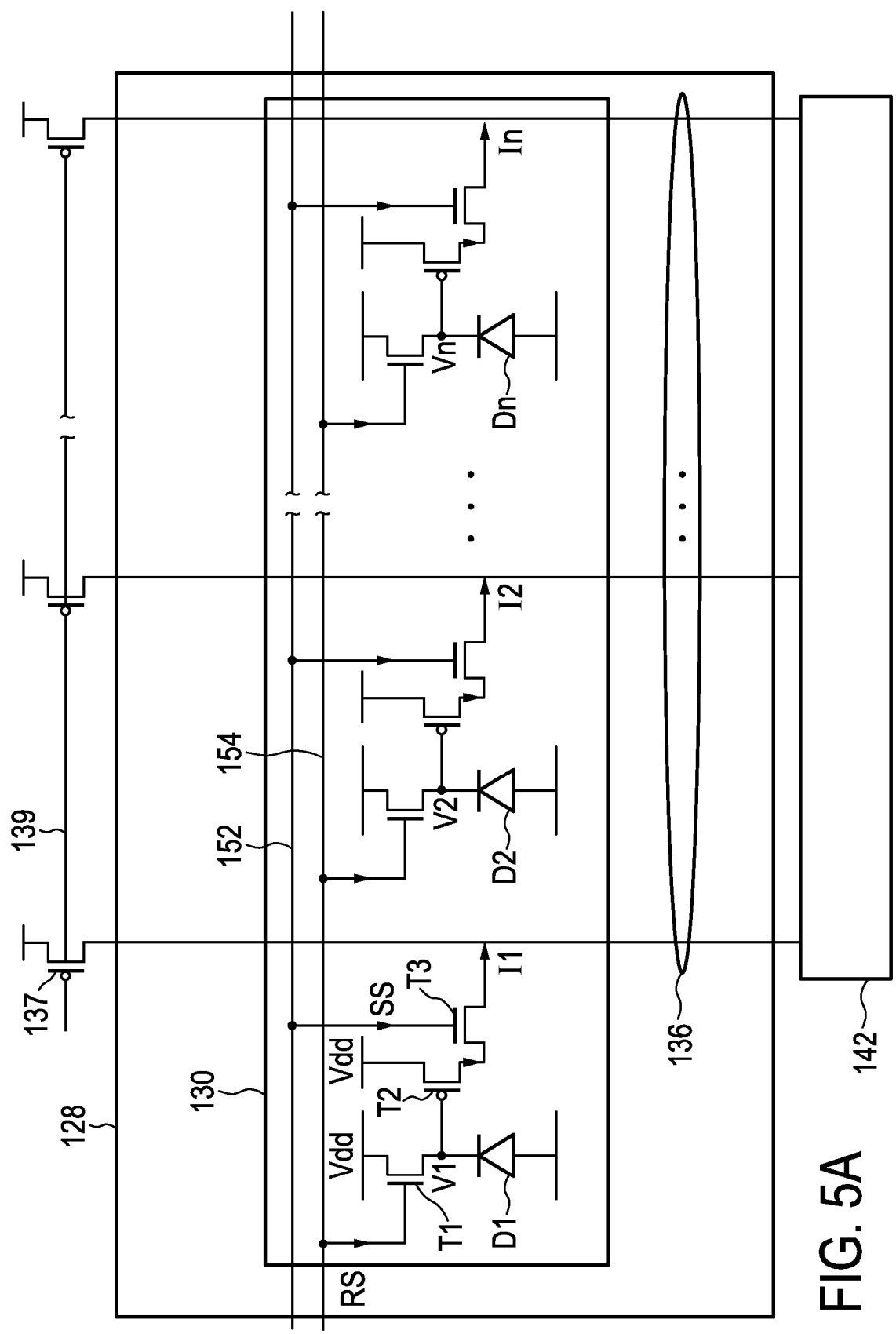
FIG. 5A shows an embodiment of the circuitry of a single pixel of a detector according to the present invention.

FIG. 5A shows an exemplary embodiment of the main circuitry of a single pixel 130 in a detector 118 according to the present invention. Exemplarily, three detection elements D1, D2, Dn are shown of the pixel 130 having in total a number of n (e.g. 16) of those detection elements arranged preferably along a row to receive the spectrally different signals or signal components emanating from a single fluorescent signal source as explained above. Those detection elements D1, D2, Dn can be photodetectors.

Concentrating on the photodetector D1 for further explanation, the photodetector D1 discharges its self capacitance over a field period. The N-type MOSFET transistor T1 is a reset switch pulsed every field period via a reset signal RS through a reset line 152 that is preferably connected to the row driver unit 132 (see FIG. 3). Thus, the reset switch T1 is pulsed every field period to recharge the capacitance of the photodiode D1.

The voltage V1 at the cathode of the photodiode T1 is connected to the gate of P-type MOSFET transistor T2, which acts as a voltage-to-current converter. If the photodetector D1 is receiving a lot of photons there will be more discharge, and therefore the gate-source voltage of transistor T2 will be larger. Therefore, it will output more current as it is biased in its saturation region.

The output current I1 of transistor T2 is fed to the winner take all circuit 142 by the N-type MOSFET transistor T3, which acts as a selection switch. Said selection switch T3 is pulsed on via a selection signal SS through select line 154, i.e. the selection switch T3 is pulsed on at the end of the field period for that row of pixels and for all detection elements within the pixels of said row. Thus, the currents I1 to In derived from the detection signals (i.e. the voltages V1 to Vn) generated by said photodetectors D1 to Dn are provided to the winner take all circuit 142 in parallel over the column bus 136. The bus lines of the column bus 136 can be separately switched on and off by separate bus line switches 137 which are controlled via a bus line address bus 139.

It shall be noted that the reset line 152 and the select line 154 correspond to the row address bus 138 shown in FIG. 4.

Figure 5B:
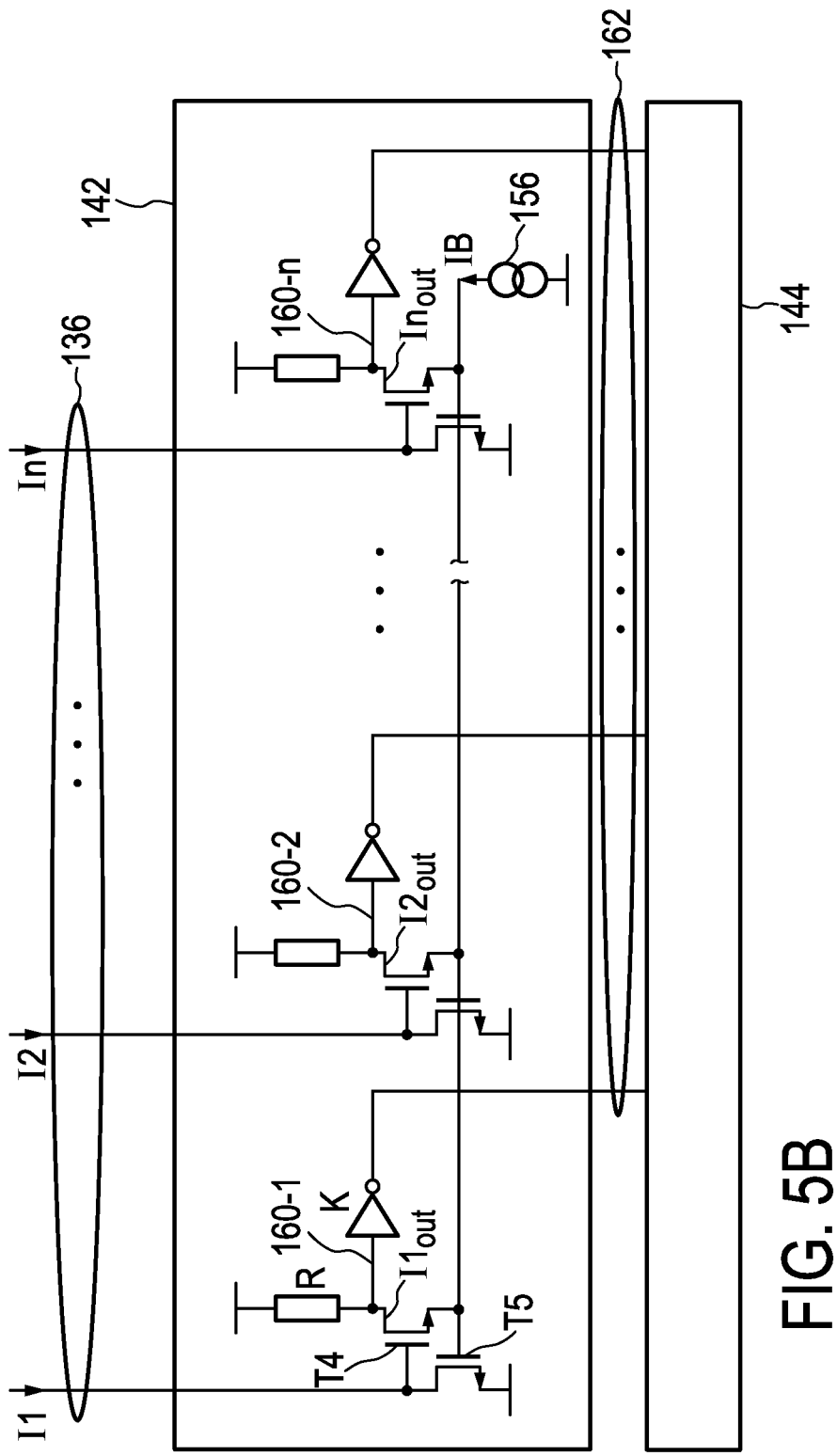
FIG. 5B shows an embodiment of the circuitry of a winner take all circuit according to the present invention.

In FIG. 5B an embodiment of the circuitry of the winner take all circuit 142 for this column of pixels is shown, to which said currents I1 to In are provided via the column bus 136. The winner take all circuit 142 comprises, in this exemplary embodiment, n pairs of N-type MOSFET transistors T4, T5. Further, a bias current source 156 for generating and drawing a bias current IB through the transistors T4 of all n pairs of transistors T4, T5 is provided. This bias current IB also sets a gate voltage for the transistor T5 which in turn sets the current that can flow through it at a fixed value.

The pair of transistors (among the n pairs of transistors) of the winner take all circuit 142 that has the highest input current, i.e. to which the highest current I1 to In (i.e. the highest luminance) is provided, then creates the highest drain voltage on the transistor T5 whose drain is provided with the current I1 from the associated photodiode D1. The drain of the transistor T5 is also connected to the gate of the transistor T4. The higher gate voltage on the transistor T4, following a higher drain voltage caused by the highest input current, then causes more current to flow in the transistor T4. As the current through the transistor T4 is, however, fixed by the bias current IB, this extra current is obtained at the expense of the other transistors T4 of the other pairs of transistors T4, T5. Therefore, the gate voltage of the transistor T4 of the other pairs falls, and a chain reaction is set off, whereby all the bias current IB must flow through only one of the transistors T4, i.e. that one transistor T4 that has the largest current flowing through its corresponding transistor T5. Hence, this pair is the "winner" delivering a high intermediate output signal $I1_{out}$ (also referred to as detector element output signal) at its intermediate output line 160-1, whereas the other intermediate output signals $In_{out}$ on the other intermediate output lines 160-n have a low amplitude.

The intermediate output signals $I1_{out}$-$In_{out}$ are converted to voltage by a resistor R, and the outputs are defined digitally by an inverter K. The resulting signal is then outputted via a pixel output bus 162, which can have n lines in parallel or which can be a multiplexed bus, to the bit (digital) conversion unit 144. Therein, the output signals are converted into a digital pixel output signal as explained above.

Figure 6:
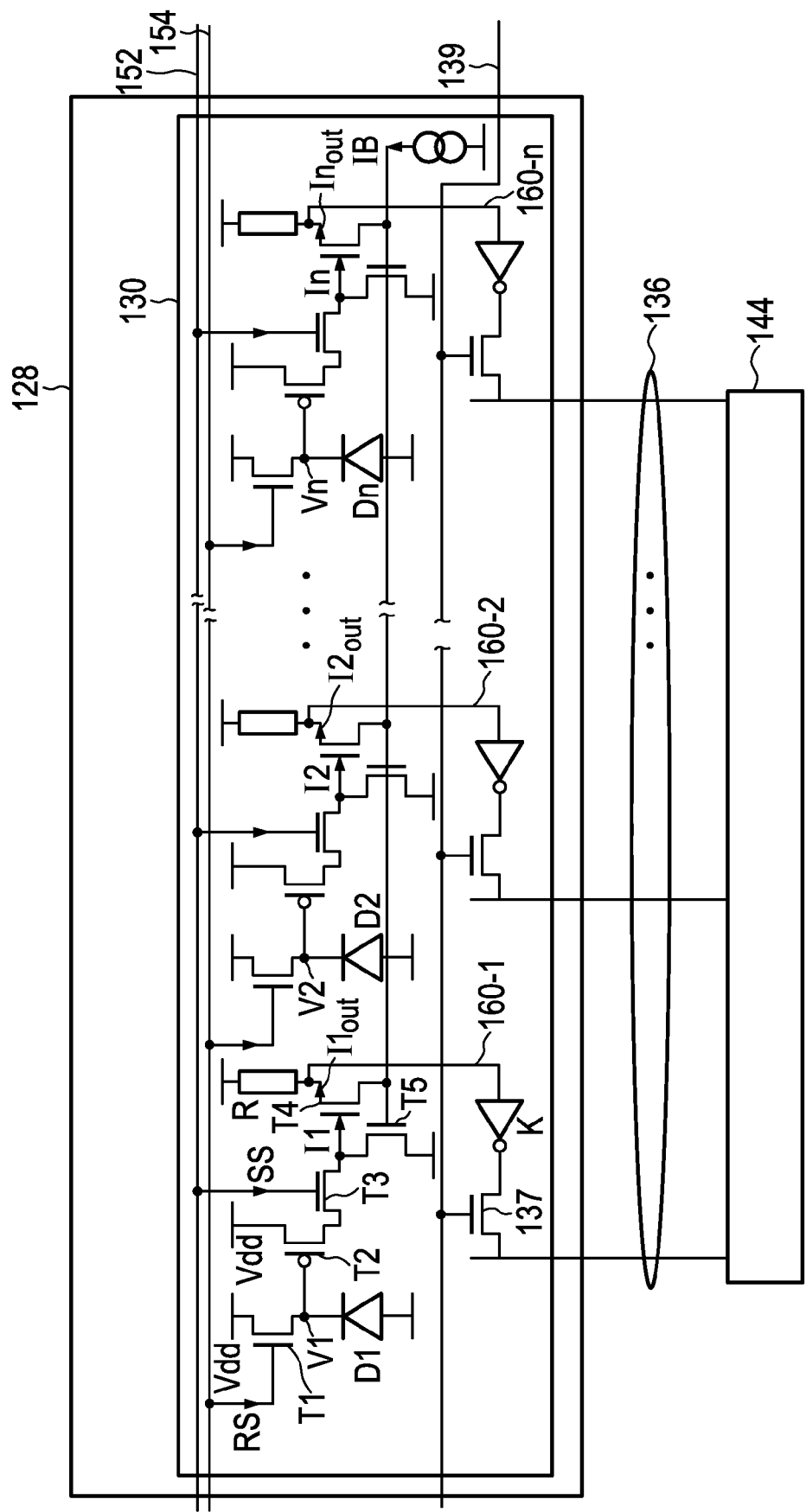
FIG. 6 shows another embodiment of the circuitry of a single pixel including a winner take all circuit according to the present invention.

FIG. 6 shows another embodiment of the circuitry of a pixel 130, according to which the winner take all circuit is part of the pixel itself rather than part of the column driver unit 134 as in the embodiment shown in FIGS. 4 and 5. The general layout of the circuitry of the pixel and the winner take all circuit is identical as in the embodiment shown in FIGS. 4 and 5. The winning current is again fed to a resistor R which creates a voltage that is either high or low. The resistor R is followed by an inverter K which gives a well defined high or low. This signal drives the column on the column bus 136.

Hence, according to this embodiment there is no winner take all circuit within the column driver unit 134. The data is fed straight to bit conversion unit 144. This should give rapid pixel readout, but the pixel has become more complicated compared to the embodiment shown in FIGS. 4 and 5.

Figure 7:
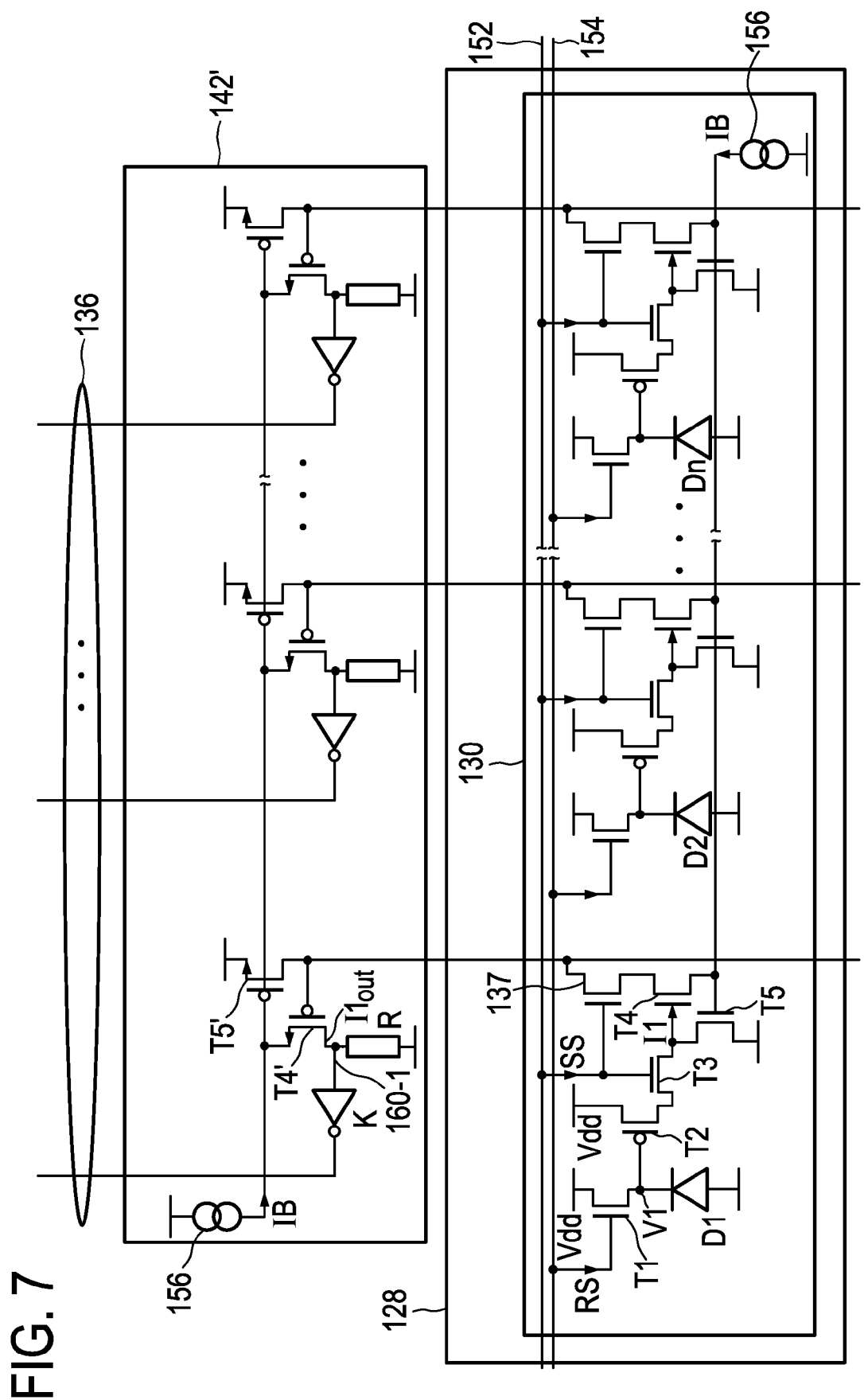
FIG. 7 shows another embodiment of the circuitry of a single pixel including a winner take all circuit coupled to an external winner take all circuit according to the present invention.

FIG. 7 shows still another embodiment according to which both the pixel 130 and the column driver circuit 134 both have a winner take all circuit, i.e. which is a hybrid of the embodiments shown in FIGS. 4 and 5 and FIG. 6. However, the winner take all circuit 142' in the column driver unit 134 is now P-type, i.e. having P-type MOSFET transistors T4' and T5', to match with the in-pixel n-type winner take all circuit having N-type MOSFET transistors T4 and T5. This embodiment is thus a kind of trade off resulting in a simple pixel circuitry, but also providing a fast readout. The outputs of the winner take all circuit 142' go to bit conversion unit 144.

As the column will have a large capacitance small current differences are not immediately transferred to the winner take all circuit 142' in the column driver unit 134. Therefore, the embodiment shown in FIGS. 5A and 5B may be less rapid than is ideal. An in-pixel winner take all circuit as provided in the embodiment shown in FIG. 6 rapidly creates a large current difference at the pixel which initially, when transferred across the column to the winner take all circuit 142' in the column driver unit 134, will be a small current difference. This winner take all circuit 142' however rapidly amplifies this small difference to create a decision more rapidly than the circuit shown in FIGS. 5A and 5B.

By the present invention high field rates can be obtained and a large number of pixels can be simultaneously read out. In particular, a plurality of discrete fluorescence signal sources can be monitored. The invention thus overcomes the limits of current detectors which are based on the CCD technology which, when applied in DNA sequencing systems, are rapidly taken to their operating limits in terms of speed of operation. The present invention can be applied in such DNA sequencing systems to monitor very fast discrete fluorescent signals. For instance, one molecule of single stranded DNA can potentially have bases incorporated by their polymerase at a rate of 10 to 100 per second. These events, which occur randomly in time, can be captured by the detector according to the present invention which has a sufficiently high readout rate of e.g. 1 kHz. Each sequencing site will have one molecule of DNA that is processed, and the currently used number of 3000 sites can be increased. The proposed in-pixel data compression and analog-to-digital conversion enables the detector to be built such that it will be both large in number of pixels (i.e. can image many sequencing sites) and very fast as the readout of digital values from a pixel on a large array can be performed very much faster than analog data.

It shall be noted that sequencing in the context of the present invention and its embodiments is not limited to DNA but also relates to sequencing where the end goal is to detect the base pairs of a nucleic acid, for example RNA, PNA, LNA.

While the invention has been illustrated and described in detail in the drawings and foregoing description, such illustration and description are to be considered illustrative or exemplary and not restrictive; the invention is not limited to the disclosed embodiments. Other variations to the disclosed embodiments can be understood and effected by those skilled in the art in practicing the claimed invention, from a study of the drawings, the disclosure, and the appended claims.

In the claims, the word "comprising" does not exclude other elements or steps, and the indefinite article "a" or "an" does not exclude a plurality. A single element or other unit may fulfill the functions of several items recited in the claims. The mere fact that certain measures are recited in mutually different dependent claims does not indicate that a combination of these measured cannot be used to advantage.

Any reference signs in the claims should not be construed as limiting the scope.

The invention claimed is:

1. A device for monitoring a plurality of discrete fluorescent signals, the device comprising:
   a substrate having a plurality of discrete fluorescent signal sources disposed thereon;
   an excitation illumination source;
   a detector for detecting fluorescent signals from the plurality of fluorescent signal sources; and an optical train positioned to simultaneously direct excitation illumination from the excitation illumination source to said plurality of discrete fluorescent signal sources on the substrate, and to direct fluorescent signals from the plurality of fluorescent signal sources to the detector, wherein said detector comprises:

a plurality of pixels for individually detecting said fluorescent signals from the plurality of fluorescent signal sources, each pixel comprising at least two detection elements, separated and spaced apart from each other, each detection element being arranged for detecting a received fluorescent signal and in response thereto for generating a detection signal, wherein the at least two detection elements of each pixel are configured to detect different principal wavelengths than each other, and a signal conversion circuit for receiving said detection signals from said at least two detection elements and for generating a pixel output signal for each pixel indicating which of said at least two detection elements which are configured to detect different principal wavelengths than each other generated the strongest detection signal.

2. The device of claim 1, wherein each pixel comprises at least four detection elements.

3. The device of claim 1, wherein said signal conversion circuit is adapted for generating a digital pixel output signal.

4. The device of claim 1, wherein said plurality of pixels are arranged as an array along columns and rows, and wherein said detector further comprises addressing and readout means for individually addressing and reading out said pixel output signals from said pixels.

5. The device of claim 4, wherein said addressing and readout means comprises a selection switch associated with each detection element which can be switched on and off by use of a selection switch addressing signal for enabling the forwarding of the output signal generated by the associated detection element to the signal conversion circuit.

6. The device of claim 4, wherein said addressing and readout means comprises a reset switch for each detection element which can be switched on and off by use of a reset signal for resetting the detection element after each detection period.

7. The device of claim 4, wherein said addressing and readout means comprises a voltage-to-current conversion element associated with each detection element for converting the detection signal of said associated detection element into a detector current signal.

8. The device of claim 7, wherein said voltage-to-current conversion element comprises a P-type MOSFET transistor whose gate is coupled to the output of the associated detection element.

9. The device of claim 1, wherein said signal conversion circuit comprises a winner take all circuit.

10. The device of claim 9, wherein said winner take all circuit comprises, for each connected detection element, a first N-type MOSFET transistor, whose drain terminal is provided with a detector current signal representing the detection signal detected by said detection element, whose source terminal is coupled to a reference potential and whose gate terminal is provided with a predetermined bias current (IB), and a second N-type MOSFET transistor, whose gate terminal is coupled to the drain terminal of the first N-type MOSFET transistor, whose source terminal is coupled to the gate terminal of the first N-type MOSFET transistor and is provided with said predetermined bias current and whose drain terminal is outputting a detector element output signal.

11. The device of claim 9, wherein said winner take all circuit is arranged external to an area of the plurality of pixels.

12. The device of claim 9, wherein said winner take all circuit is arranged within an area of the plurality of pixels.

13. The device of claim 9, wherein for each pixel two winner take all circuits are associated, wherein a first winner take all circuit is arranged external to the area of the plurality of pixels and a second winner take all circuit is arranged within the area of the plurality of pixels.

14. The device of claim 1, wherein said optical train comprises an objective lens focused in a first focal plane at the substrate, for simultaneously collecting fluorescent signals from the plurality of fluorescent signal sources on the substrate, a spectral separation means for spatially separating spectral components of the fluorescence signals, and a focusing lens for receiving the spatially separated spectral components of the fluorescent signals and focusing them onto the detector, wherein the optical train provides each of at least two of the spatially separated spectral components to a corresponding one of the at least two detection elements of which are configured to detect different principal wavelengths than each other.

15. The device of claim 1, wherein each of the discrete fluorescent signal sources emits a fluorescent signal having one of the principal wavelengths.

16. The device of claim 1, wherein each pixel comprises four detection elements, wherein each detection element is configured to detect a corresponding one of four principal wavelengths which are all different from each other, and wherein the signal conversion circuit is configured to receive the detection signals from the four detection elements and to generate the pixel output signal for each pixel indicating which of the four detection elements, which are each configured to detect a different one of the four principal wavelengths than each other, generated the strongest detection signal.

17. The device of claim 16, wherein each of the discrete fluorescent signal sources emits a fluorescent signal having one of the four principal wavelengths.

18. The device of claim 17, wherein said optical train comprises:

an objective lens focused in a first focal plane at the substrate, for simultaneously collecting fluorescent signals from the plurality of fluorescent signal sources on the substrate;

a spectral separation means for spatially separating at least four spectral components of the fluorescence signals, at least four of the spectral components each of the having one of the four principal wavelengths; and a focusing lens for receiving the spatially separated spectral components of the fluorescent signals and focusing them onto the detector, wherein the optical train provides each of the four spatially separated spectral components to a corresponding one of the four detection elements which are configured to detect a different one of the four principal wavelengths than each other.

19. A detector for detecting fluorescent signals from a plurality of fluorescent signal sources for use in a device for monitoring a plurality of discrete fluorescent signals, said device comprising a substrate having a plurality of discrete fluorescent signal sources disposed thereon; an excitation illumination source; and an optical train positioned to simultaneously direct excitation illumination from the excitation illumination source to said plurality of discrete fluorescent signal sources on the substrate, and to direct fluorescent signals from the plurality of fluorescent signal sources to the detector, said detector comprising:

a plurality of pixels for individually detecting said fluorescent signals from the plurality of fluorescent signal sources, each pixel comprising at least two detection elements separated and spaced apart from each other, each detection element being arranged for detecting a received fluorescent signal and in response thereto for generating a detection signal, wherein the at least two detection elements are configured to detect different principal wavelengths than each other, and a signal conversion circuit for receiving said detection signals from said at least two detection elements and for generating a pixel output signal for each pixel indicating which of said at least two detection elements which are configured to detect different principal wavelengths than each other generated the strongest detection signal.

20. The detector of claim 19, wherein each pixel comprises four detection elements, wherein each detection element is configured to detect a corresponding one of four principal wavelengths which are all different from each other, and wherein the signal conversion circuit is configured to receive the detection signals from the four detection elements and to generate the pixel output signal for each pixel indicating which of the four detection elements, which are each configured to detect a different one of the four principal wavelengths than each other, generated the strongest detection signal.

* * * * *